(12) United States Patent
Shinada et al.

(10) Patent No.: US 9,784,714 B2
(45) Date of Patent: Oct. 10, 2017

(54) DISCHARGE IONIZATION CURRENT DETECTOR AND TUNING METHOD FOR THE SAME

(71) Applicant: SHIMADZU CORPORATION, Kyoto-shi, Kyoto (JP)

(72) Inventors: Kei Shinada, Uji (JP); Shigeyoshi Horiike, Uji (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 229 days.

(21) Appl. No.: 14/766,914

(22) PCT Filed: Feb. 15, 2013

(86) PCT No.: PCT/JP2013/053659

§ 371 (c)(1),
(2) Date: Aug. 10, 2015

(87) PCT Pub. No.: WO2014/125610

PCT Pub. Date: Aug. 21, 2014

(65) Prior Publication Data

US 2015/0369777 A1    Dec. 24, 2015

(51) Int. Cl.
*G01N 27/70* (2006.01)
*G01N 30/64* (2006.01)

(52) U.S. Cl.
CPC .............. *G01N 27/70* (2013.01); *G01N 30/64* (2013.01)

(58) Field of Classification Search
CPC ................................ G01N 27/70; G01N 30/64
USPC ............... 324/464–470; 204/157.44, 157.63; 205/775, 789
See application file for complete search history.

(56) References Cited

U.S. PATENT DOCUMENTS

2009/0090176 A1    4/2009  Toribio et al.
2011/0316551 A1    12/2011 Shinada et al.

FOREIGN PATENT DOCUMENTS

| EP | 1 703 541 | 9/2006 |
| JP | 2006-261116 | 9/2006 |
| JP | 2007-218843 | 8/2007 |
| JP | 2007-315853 | 12/2007 |
| JP | 2008-4673 | 1/2008 |
| JP | 2010-60354 A | 3/2010 |

(Continued)

OTHER PUBLICATIONS

Written Opinion for PCT/JP2013/053752 dated Mar. 19, 2013. [PCT/ISA/237].

(Continued)

*Primary Examiner* — Melissa Koval
*Assistant Examiner* — Rahul Maini
(74) *Attorney, Agent, or Firm* — Sughrue Mion, PLLC (57) ABSTRACT

An adjusting method for a discharge ionization current detector of the present invention is provided for a discharge ionization current detector for a gas chromatograph, which improves the precision and reproducibility of measurements results of the detector. The discharge ionization current detector adjusts at least one of purity of introduced helium gas, a flow rate of the introduced helium gas, an amplitude of voltage of the low-frequency dielectric barrier discharge, and a frequency of the voltage of the low-frequency dielectric barrier discharge so that intensity of light having a wavelength of 640 nm reaches the maximum in a range of wavelengths of 250 to 700 nm with respect to light emitted by the helium plasma.

7 Claims, 6 Drawing Sheets

(56) References Cited

FOREIGN PATENT DOCUMENTS

| JP | 2011-117854 | A | 6/2011 |
|----|-------------|---|--------|
| JP | 2011-158357 | A | 8/2011 |
| JP | 2011-232071 | A | 11/2011 |
| JP | 2012-8088 | A | 1/2012 |
| JP | 2013-3070 | | 1/2013 |
| WO | 2012169419 | A1 | 12/2012 |

OTHER PUBLICATIONS

International Written Opinion for PCT/JP2013/053659, dated Mar. 19, 2013 [PCT/ISA/237].
International Search Report for PCT/JP2013/053752 dated Mar. 19, 2013 [PCT/ISA/210].
International Search Report of PCT/JP2013/053659, dated Mar. 19, 2013. [PCT/ISA/210].
Communication dated Jun. 16, 2017 from the United States Patent and Trademark Office in U.S. Appl. No. 14/767,191.
English Machine Translation of Hidetaka et al, JP 2007-315853 A, Dec. 6, 2007, Translated Jun. 2017.

DISCHARGE IONIZATION CURRENT DETECTOR AND TUNING METHOD FOR THE SAME

CROSS REFERENCE TO RELATED APPLICATIONS

This application is a National Stage of International Application No. PCT/JP2013/053659 filed Feb. 15, 2013, the contents of all of which are incorporated herein by reference in their entirety.

TECHNICAL FIELD

The present invention relates to a discharge ionization current detector that is primarily suitable as a detector for a gas chromatograph (GC), and a tuning method for the same, and more specifically relates to the improvement in precision and reproducibility of measurement results of the detector.

BACKGROUND ART

As a detector for GC, detectors of various types have been conventionally in practical use, such as a pulsed discharge detector (PDD), and a low-frequency dielectric barrier discharge ionization detector (BID), in which electric discharge is utilized, besides a flame ionization detector (FID), and a thermal conductivity detector (TCD), and an electron capture detector (ECD).

Among the aforementioned detectors, the FID is generally used in order to detect organic substances. The FID ionizes sample components in sample gas with hydrogen flames and detects a resultant ion current. The FID has the characteristic of a wide dynamic range, but has low sensitivity with respect to incombustible gas and inorganic gas, and therefore compounds to be analyzed are limited because the sample is burned in the hydrogen flame to ionize the sample components.

In the PDD, helium gas or the like is excited by electric discharge through the application of high-voltage pulses to electrodes, thereby plasma is generated, and a sample is ionized by utilizing the emission of light (vacuum ultraviolet light and the like) of the plasma. The PDD has high sensitivity with respect to the incombustible gas and the inorganic gas, and is suitable for detecting almost all compounds with which the gas chromatograph is required to cope. However, the dynamic range of the PDD is smaller than that of the FID. The reason is assumed that, in the PDD, electric discharge is unstable and the state of plasma tends to fluctuate (for example, see Patent Literature 1).

In contrast, in the BID, a space surrounded by a dielectric substance is provided, and an alternating-current low-frequency voltage is applied to a discharge electrode formed on the outside of the dielectric substance, thereby plasma is generated in the space. Thus, in the BID, the electric discharge is stabilized, and the fluctuations in the state of the plasma are suppressed, compared with the PDD. The reason is assumed as follows. The discharge electrode and the plasma are separated by the dielectric barrier (synthetic quartz or the like), which prevents the discharge electrode from being exposed to the plasma, and emission of spattered particles or absorbed gas molecules can be prevented. And the plasma generated by the low-frequency voltage (having frequency of about 5 to 50 kHz, and amplitude of several kilo-volts) has low temperature compared with a case where the plasma is generated by a high-voltage pulse (having frequency of several megahertz, and amplitude of several kilovolts) of the PDD, so that the generation of impurities of gas caused by the heating of the inner-wall material of the detector can be suppressed. As a result, the BID excels in stability, and a favorable signal-to-noise (S/N) ratio can be obtained for a long period of time (for example, see Patent Literatures 1 to 5).

CITATION LIST

Patent Literature

Patent Literature 1: JP 2011-117854 A
Patent Literature 2: JP 2011-158357 A
Patent Literature 3: JP 2011-232071 A
Patent Literature 4: JP 2012-8088 A
Patent Literature 5: JP 2010-60354 A

SUMMARY OF INVENTION

Technical Problem

As described above, the stabilization of the electric discharge is essential in the discharge ionization current detector. In the BID, the comparatively stabilized electric discharge is obtained as described above, but the fluctuation in detection results is observed in practical use due to various factors, which deteriorates the precision and reproducibility of measurements.

The present invention has been achieved to solve the above-mentioned problems, and it is an object of the present invention to provide a discharge ionization current detector that can prevent the deterioration in the precision and reproducibility of measurements.

Solution to Problem

The state of electric discharge may change by the minuscule amount of impurity included in the helium gas, so that it is recommended that gas having high purity is used, for example, in the PDD. However, it is difficult to control the amount of impurities mixed due to various factors at all times. Accordingly, the direct measurement of the amount of the vacuum ultraviolet light, by which the sample is ionized, is ideal in order to maintain the stability of performance of the detector. However, it is necessary to use the large-size, high-priced vacuum ultraviolet spectrometer in order to directly measure the vacuum ultraviolet light having a wavelength of 200 nm or shorter.

The inventors of the present invention made various experiments and found that, regarding the plasma generated by exciting helium gas by means of electric discharge, the emission state of the vacuum ultraviolet light can be determined based on the emission spectrum in a range of wavelengths of 250 to 700 nm, which are longer than the wavelength of the vacuum ultraviolet light (wavelength of 10 to 200 nm).

The emission spectrum of the helium plasma in the BID includes, in the wavelength range of 250 to 700 nm, the component of 640 nm, which is the emission line of the helium molecular ion ($He_2^+$), and the components of 588 nm and 707 nm, which are the emission lines of the helium atom. In addition, the emission spectrum includes the component of 533 nm and 544 nm, which are the emission of the oxygen molecule, the component of 656 nm, which is the emission of the hydrogen atom, and others, as impurities. Here, the helium molecular ion ($He_2^+$) is generated by the collision of helium atoms in the helium plasma, and its generation is mainly performed by three-body collision described below. First, an unstable helium molecule (He$_2$) is generated by two-body collision, and another helium atom collides the helium molecule (He$_2$) in a short period of time during which the helium molecule (He$_2$) exists. This is the process of generating a stable helium molecule ion (He$_2^+$). The frequency of the aforementioned three-body collision exponentially decreases as the concentration of impurities in the helium plasma increases (that is, decreases in proportion to the cube of the concentration). For this reason, even when impurities are in minute quantity, the intensity of the emission line at a wavelength of 640 nm with respect to light emitted by the helium plasma is small and unstable.

This means that the intensity of the emission line at the wavelength of 640 nm with respect to the helium molecular ion (He$_2^+$) can serve as an indicator of the existence of the minute quantity of impurities in the helium plasma, and thus the emission state of the vacuum ultraviolet light.

With this new findings that the intensity of the emission line at the wavelength of 640 nm serves as the indicator, which has been unknown heretofore, the inventors of the present invention have further examined and found that the helium plasma having emission spectrum in which the intensity at the wavelength of 640 nm is higher than that at other wavelengths in a range of 250 to 700 nm emits stable and strong vacuum ultraviolet light.

That is, with respect to a discharge ionization current detector configured to utilize helium plasma generated by low-frequency dielectric barrier discharge, a tuning method for the discharge ionization current detector according to the present invention includes adjusting at least one of purity of introduced helium gas, a flow rate of the introduced helium gas, an amplitude of voltage of the low-frequency dielectric barrier discharge and a frequency of the voltage of the low-frequency dielectric barrier discharge so that intensity of light having a wavelength of 640 nm reaches the maximum in a range of wavelengths of 250 to 700 nm with respect to light emitted by the helium plasma.

With this tuning method, the intensity (the intensity of the emission line) of light having the wavelength of 640 nm reaches the maximum in a range of wavelengths of 250 to 700 nm, with respect to light emitted by the helium plasma, by adjusting the purity or the flow rate of the helium gas introduced, or the amplitude or frequency of the voltage of the low-frequency dielectric barrier discharge. Such tuning is feasible because these conditions influences the intensity of the emission line at the wavelength of 640 nm. The purity of the introduced helium gas is associated with the concentration of impurities in the helium plasma, which influences the amount of helium molecular ions (He$_2^+$) generated by the three-body collision of the helium atoms, that is, the intensity of the emission line at the wavelength of 640 nm. Also, the flow rate of the introduced helium gas is associated with the number density of the helium (the unit is represented, for example, as "atoms/cm$^3$"), which influences the intensity of the emission line at the wavelength of 640 nm. Furthermore, the amplitude and the frequency of the voltage of the low-frequency dielectric barrier discharge are associated with the excitation power that generates the helium plasma, which influences the emission state of the helium plasma, that is, the intensity of the emission line at the wavelength of 640 nm.

Also, a discharge ionization current detector corresponding to the aforementioned tuning method utilizes helium plasma generated by low-frequency dielectric barrier discharge and includes:

a) a helium gas introducing section configured to introduce helium gas, b) a voltage adjusting section configured to adjust an amplitude or a frequency of low-frequency voltage applied to a discharge electrode used for the low-frequency dielectric barrier discharge, c) a light detecting section configured to detect intensity of light for every wavelength in a range of wavelengths of 250 to 700 nm, with respect to light emitted by the helium plasma, and d) a control section configured to control the voltage adjusting section in such a manner that intensity of light having a wavelength of 640 nm reaches the maximum in the range of the wavelengths.

The purity and the flow rate of the introduced helium gas are determined in advance by experiment, but, in order to make these adjustable, the aforementioned discharge ionization current detector may further include:

e) a helium gas purity adjusting section configured to adjust purity of the helium gas introduced, and f) a helium gas flow rate adjusting section configured to adjust a flow rate of the helium gas introduced, and the control section may be configured to control at least one of the helium gas purity adjusting section and the helium gas flow rate adjusting section in such a manner that the intensity of the light having the wavelength of 640 nm reaches the maximum in the range of the wavelengths.

With respect to the aforementioned detector, when the purity and the flow rate of the helium gas are determined in advance, the intensity of the light having the wavelength of 640 nm can be maximized in a range of wavelengths of 250 to 700 nm, with respect to light emitted by the helium plasma, by setting in advance the amplitude and frequency of the low-frequency voltage applied to the discharge electrode used for the low-frequency dielectric barrier discharge, to appropriate conditions.

In this case, the aforementioned controller is unnecessary. The appropriate conditions of the amplitude and frequency of the voltage of the low-frequency dielectric barrier discharge can be determined in advance by experiment.

When the amplitude and frequency of the low-frequency voltage applied to the discharge electrode used for the low-frequency dielectric barrier discharge are determined in advance, the intensity of the light having the wavelength of 640 nm can be maximized in a range of wavelengths of 250 to 700 nm, with respect to light emitted by the helium plasma, further by setting in advance the purity or the flow rate of the helium gas to the appropriate conditions.

Alternatively, the aforementioned control section may further control the voltage adjusting section in such a manner that the intensity of the light having the wavelength of 640 nm remains constant.

This control makes it possible to further stabilize the emission state of the vacuum ultraviolet light.

Advantageous Effects of the Invention

According to the tuning method for the discharge ionization current detector of the present invention, helium plasma that emits stable and strong vacuum ultraviolet light is generated, compared with conventional one, so that the discharge ionization current detector having improved precision and reproducibility is obtained.

DESCRIPTION OF EMBODIMENTS

Hereinafter, embodiments of the present invention will be described referring to drawings.

Figure 1:
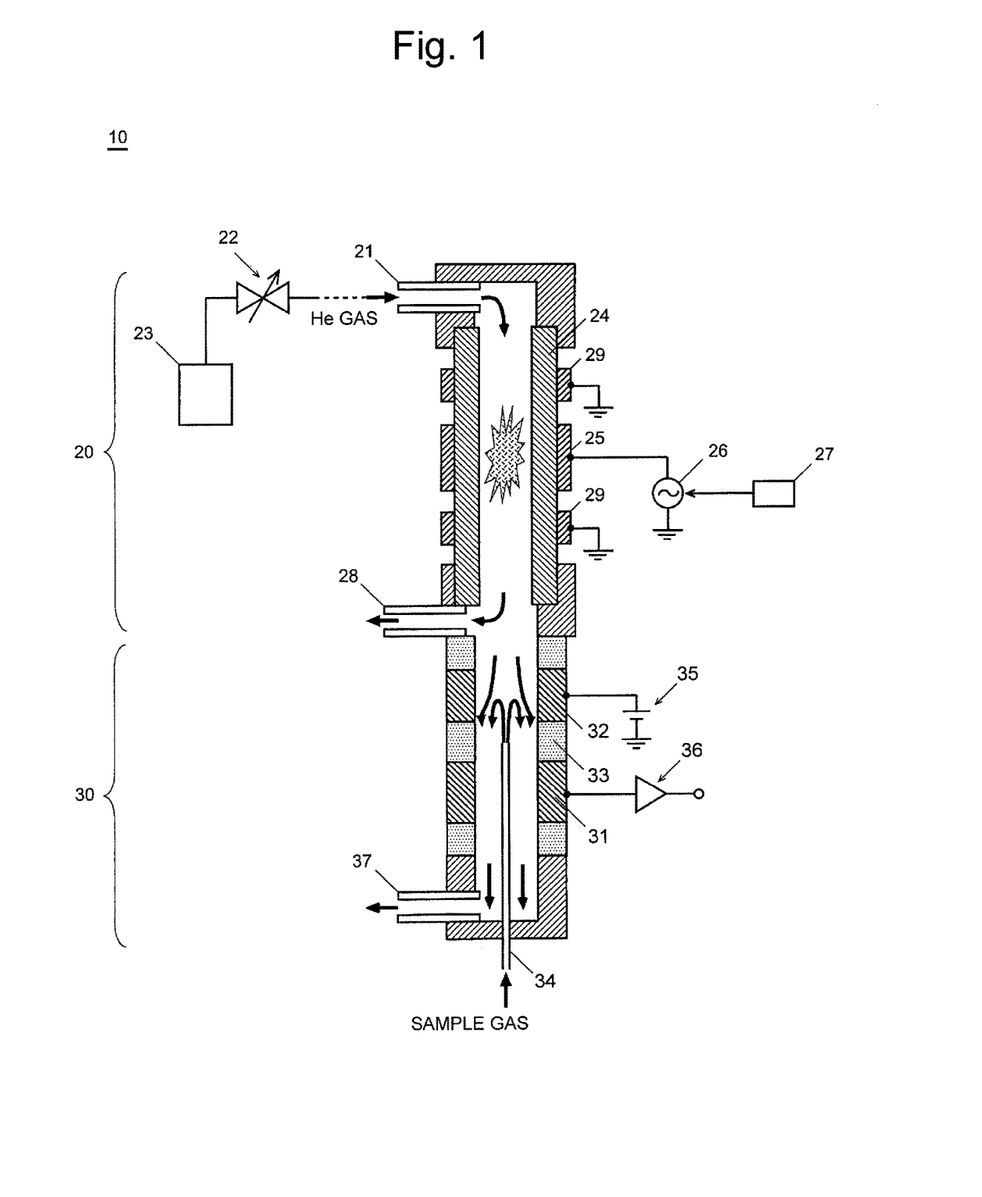
FIG. 1 is a view illustrating the schematic configuration of a discharge ionization current detector in an embodiment of the present invention.

FIG. 1 illustrates a discharge ionization current detector 10 that is tuned by a tuning method for the discharge ionization current detector of the present invention (hereinafter, sometimes merely referred to as "the present adjusting method") and the cross section of the discharge ionization current detector 10 formed in an almost cylindrical shape. The discharge ionization current detector 10 is a discharge ionization current detector according to an embodiment of the present invention and mainly constituted of a plasma generating section 20 and an ion collecting section 30.

A gas introduction port 21 for introducing helium (He) gas is provided above the plasma generating section 20, and a cylindrical pipe 24 formed of a dielectric member is provided below the gas introduction port 21. Furthermore, an exhaust port 28 for discharging the helium gas is provided below the cylindrical pipe 24. The gas introduction port 21 is connected to a helium purifier 23 via a valve 22. The helium purifier 23 removes impurities in the helium gas fed from a helium cylinder (not illustrated), supplies the high-purity helium gas purified to the gas introduction port 21. In the helium purifier 23, appropriate purity can be selected in accordance with the purity of the helium gas required. The opening degree of the valve 22 is adjusted, so that the flow rate of the helium gas fed from the helium purifier 23 to the gas introduction port 21 can be controlled, and the density of helium plasma in the interior of the plasma generating section 20 can be changed. The cylindrical pipe 24 is formed of the dielectric substance. When the dielectric substance is exposed to the helium plasma, impurities are emitted from the surface of the dielectric substance, but the emissions of the impurities can be controlled by the selection of dielectric materials. Accordingly, it is preferable that the dielectric materials of the cylindrical pipe 24 can be appropriately replaced. A discharge electrode 25 is arranged on the outer side of the cylindrical pipe 24, and an alternating-current power supply 26 is connected to the discharge electrode 25. The alternating-current power supply 26 is a low-frequency voltage application section that applies a low-frequency voltage to the discharge electrode 25. The low-frequency voltage is determined by amplitude and frequency, which are controlled by a controller 27. Grounding electrodes 29 grounded on the upstream and the downstream of the gas flow with respect to the discharge electrode 25 are arranged on the outer side of the cylindrical pipe 24.

An insulating member 33, a bias electrode 32, the insulating member 33, an ion collecting electrode 31, and the insulating member 33 are provided in the ion collecting section 30 in the order of proximity to the plasma generating section 20. With this structure, the ion collecting electrode 31 and the bias electrode 32 are insulated, and furthermore, both electrodes are insulated from a ground potential. It is preferable that the ion collecting electrode 31 and the bias electrode 32 be formed of stainless steel or nickel to prevent oxidation. The ion collecting electrode 31 is connected to an external circuit (not illustrated) via an amplifier 36, and the bias electrode 32 is connected to a direct-current power source 35. For example, aluminum oxide or sapphire having high purity is used for the insulating member 33. Furthermore, a capillary 34 for introducing sample gas is inserted from an end surface opposite to the introducing port of the helium gas and fixed in such a manner that the tip end of the capillary 34 is positioned in the vicinity of the center of the bias electrode 32. An exhaust port 37 for discharging the sample gas is also provided on the end surface opposite to the introducing port of the helium gas. It is noted that the ion collecting section 30 is provided in such a manner that the temperature thereof can be adjusted by a heat source (not illustrated) such as a heater, for the purpose of analyzing the sample having a high-boiling-point component.

Hereinafter, the basic operation of the discharge ionization current detector 10 will be described. In the plasma generating section 20, the helium gas purified by the helium purifier 23 is introduced from the gas introduction port 21 into the interior of the plasma generating section 20 via the valve 22. Also, the alternating-current power supply 26 is controlled by the controller 27, and a low-frequency alternating-current voltage having frequency ranges approximately 5 to 50 kHz, and amplitude ranges approximately 1 to several kilo-volts, is applied to the discharge electrode 25, thereby generating electric discharge between the grounding electrode 29 and the discharge electrode 25. The electric discharge is low-frequency dielectric barrier discharge where the cylindrical pipe 24 serves as a dielectric substance, and this excites the helium gas to generate helium plasma. The helium plasma emits light (mainly, vacuum ultraviolet light), and the light reaches the ion collecting section 30.

In contrast, the ion collecting section 30 is provided such that, while the external circuit inclusive of the amplifier 36 is operated, the ions collected by the ion collecting electrode 31 can be detected as an ion current. Also, a voltage is applied to the bias electrode 32 by means of the direct-current power source 35. The voltage is a direct-current voltage ranging from approximately 100 to 200 V. In this state, the sample gas is introduced by the capillary 34.

The sample gas introduced is blown out upward from the tip end of the capillary 34. Here, the vacuum ultraviolet light reached from the plasma generating section 20 is emitted to the sample gas. Accordingly, the sample gas is ionized and turned into sample ions. The sample ions are influenced by the electric fields formed by the voltage applied to the bias electrode 32 and guided to the ion collecting electrode 31 positioned below. The sample ions reached the ion collecting electrode 31 are detected as the ion current through the amplifier 36. It is noted that the sample gas flows in such a manner as to be pushed back by the helium gas, and is discharged through the exhaust port 37, hence the sample gas does not reach the plasma generating section 20.

In the discharge ionization current detector having the aforementioned constitution, the present tuning method means adjusting at least one of the purity of introduced helium gas, the flow rate of the introduced helium gas, the amplitude of the voltage of the low-frequency dielectric barrier discharge, and the frequency of the voltage of the low-frequency dielectric barrier discharge so that the intensity of light having a wavelength of 640 nm reaches the maximum in a range of wavelengths of 250 to 700 nm of the light emitted by the helium plasma. Hereinafter, its embodiment will be described.

Figure 4:
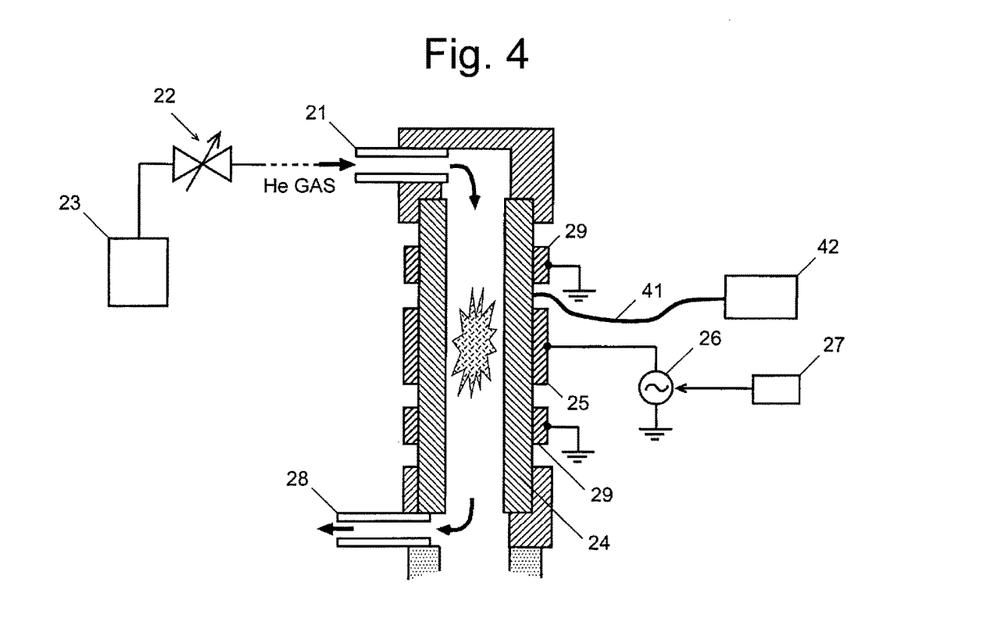
FIG. 4 is a view illustrating the schematic configuration of a plasma generating section of the discharge ionization current detector in another embodiment of the present invention.

The present tuning method includes detecting the intensity for every wavelength in a range of wavelengths of 250 to 700 nm with respect to the emission spectrum of light emitted by the helium plasma with the discharge ionization current detector. For example, as illustrated in FIG. 4, the tip end of an optical fiber 41 is mounted on the lateral surface on the outer side of the cylindrical pipe 24, and the light emitted by the helium plasma is introduced to a spectrum analyzer 42 serving as a light detecting section that optically detects the intensity of the light for every wavelength, through the optical fiber 41. Accordingly, the emission spectrum of the helium plasma is measured by use of the spectrum analyzer 42. The measurement results are, for example, displayed on a display section provided in the spectrum analyzer 42 in order for a user to verify the results. The wavelengths measured by the spectrum analyzer 42 preferably range from 250 to 700 nm. It is noted that the illustration of the ion collecting section is omitted in FIG. 4 (hereinafter, the same is applied to FIGS. 5 and 6).

Figure 7:
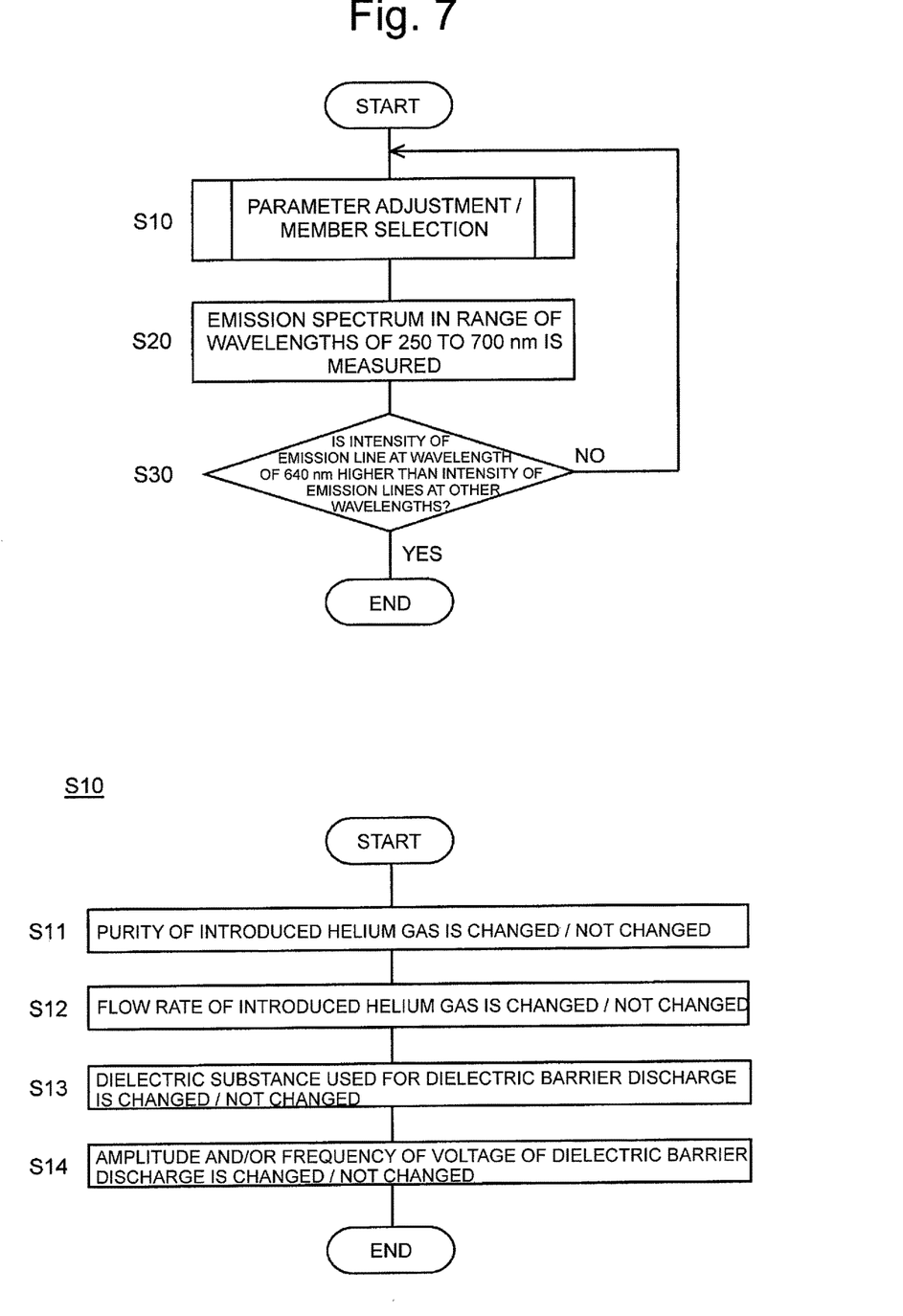
FIG. 7 is a view illustrating a flowchart of a tuning method for the discharge ionization current detector of the present invention.

With this constitution, the discharge ionization current detector is tuned in accordance with a flowchart illustrated in FIG. 7. First, a user performs the parameter adjustment/member selection of the discharge ionization current detector (Step S10). Step S10 includes the steps of changing/not changing the purity of the introduced helium gas (Step S11), changing/not changing the flow rate of the introduced helium gas (Step S12), changing/not changing the dielectric member used for the low-frequency dielectric barrier discharge (Step S13), and changing/not changing the amplitude and/or frequency of the voltage of the low-frequency dielectric barrier discharge (Step S14). For example, Step S11 can be executed by adjusting the purity of the helium gas by means of the helium purifier 23, and Step S12 can be executed by adjusting the opening degree of the valve 22, and Step S13 can be executed by replacing the dielectric materials of the cylindrical pipe 24, and Step S14 can be executed by controlling the amplitude and/or frequency of the voltage of the alternating-current power supply 26 by means of the controller 27. It is noted that the amplitude and/or frequency of the voltage of the dielectric barrier discharge in Step S14 means the amplitude and/or frequency of the low-frequency voltage applied to the discharge electrode 25.

Figure 8:
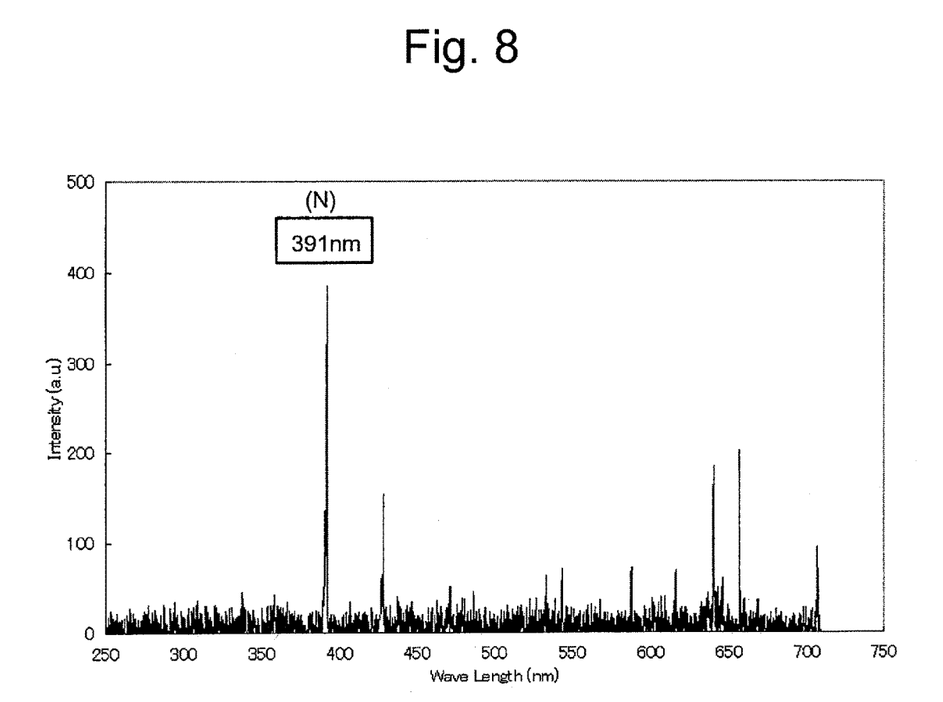
FIG. 8 is a view illustrating the emission spectrum of the helium plasma of the discharge ionization current detector before tuning by the tuning method for the discharge ionization current detector of the present invention.

The emission spectrum in a range of wavelengths of 250 to 700 nm is measured, with respect to the light emitted by the helium plasma after the aforementioned parameter adjustment/member selection are performed (Step S20). The user verifies the measurement results and determines whether or not the intensity of the emission line at the wavelength of 640 nm is higher than (that is, the maximum) the intensity of the emission lines at other wavelengths (Step S30). When it is determined that the intensity of the emission line is not the maximum, the parameter adjustment/member selection are performed again (Step S10). In this time, at the Step S10, adjustment is made in consideration of the measurement results of the emission spectrum. For example, regarding the emission spectrum, when the emission line (at the wavelength of 656 nm) of a hydrogen atom or the emission lines (at the wavelengths of 533 nm and 544 nm) of an oxygen atom distinctly appears, the dielectric member having a lower hydroxyl group (OH) content is provided (Step S13), and when the emission line at a wavelength other than the emission line of the hydrogen atom or the oxygen atom distinctly appears, adjustment is made so as to raise the purity of the introduced helium gas (Step S11). For example, spectrum data illustrated in FIG. 8 represents a case where spectrum is measured immediately after a helium gas pipe is connected to the detector. The emission line (at the wavelength of 391 nm) of nitrogen distinctly appears, which means that replacement of the air mixed in the inner wall of the pipe or the connection portion is not sufficiently made yet, or that slight leakage is caused in the connection portion. It is necessary to ensure the time required for replacement, or locate the leakage point and deal with the leakage accordingly. Also, when the intensity of the emission line (at the wavelength of 640 nm) of a helium molecular ion ($He_2^+$) is absolutely low, adjustment is made so as to increase the flow rate of the introduced helium gas (Step S12), or adjustment is made so as to increase the amplitude and/or frequency of the voltage of dielectric barrier discharge (Step S14).

Then, the emission spectrum is measured again (Step S20). The aforementioned operations are repeated, and at a time point when the intensity of the emission line at the wavelength of 640 nm becomes higher than that of the emission lines at other wavelengths, the adjustment is completed.

Thus, the discharge ionization current detector is tuned in such a manner that the intensity of light having a wavelength of 640 nm reaches the maximum in a range of wavelengths of 250 to 700 nm, with respect to the light emitted by the helium plasma.

When the discharge ionization current detector is tuned by the aforementioned tuning method, it is verified that, for example, under the following conditions, the intensity of light having a wavelength of 640 nm reaches the maximum in a range of wavelengths of 250 to 700 nm, with respect to the light emitted by the helium plasma. First, a helium purifier that purifies the helium gas having the impurity concentration of 10 bbp or less is employed as the helium purifier 23. Next, the opening degree of the valve 22 is changed, and the flow rate of the introduced helium gas is adjusted so that the helium gas in the interior of the plasma generating section 20 can be replaced on in about 0.05 to 2 seconds. Hence, the density of the helium plasma depends on values of the flow rate. Furthermore, the cylindrical pipe 24 is formed of synthetic quartz glass having a hydroxyl group (OH) content of 10 ppm or less. Finally, the alternating-current power supply 26 is controlled by the controller 27 so as to apply the alternating-current voltage having the amplitude of 1 to 10 kV, and frequency of 1 to 50 kHz to the discharge electrode 25. It is noted that the cylindrical pipe 24 may be formed of dielectric members made of sapphire glass or high-purity aluminum oxide.

Figure 2:
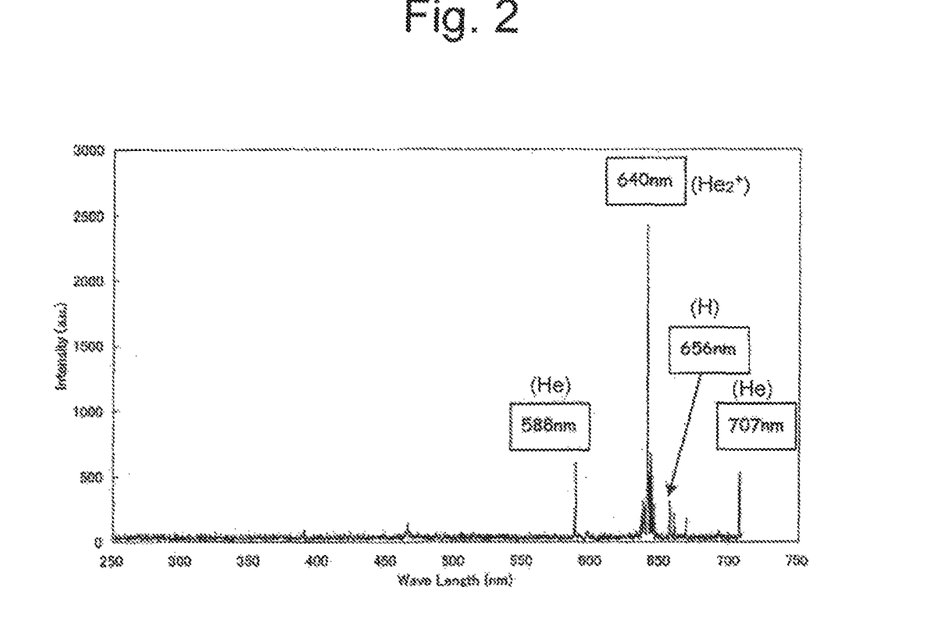
FIG. 2 is a view illustrating the emission spectrum of helium plasma generated in the discharge ionization current detector in the embodiment of the present invention.

FIG. 2 illustrates the emission spectrum of the helium plasma generated under the aforementioned conditions. A horizontal axis represents wavelengths (nm), and a vertical axis represents the intensity of spectrum (arbitrary unit). In the emission spectrum, the emission line (at the wavelength of 656 nm) of the hydrogen atom that is impurity emerges besides the emission lines (at the wavelengths of 588 nm and 707 nm) of the helium atom and the emission line (at the wavelength of 640 nm) of the helium molecular ion ($He_2^+$). Also, the intensity of the emission line at the wavelength of 640 nm larger and more dominant than that of the emission lines at other wavelengths. This represents the stable generation of the helium molecular ion ($He_2^+$) by the three-body collision of the helium atoms, and it is evident that thus generated helium plasma has a low impurity concentration and emits stable vacuum ultraviolet light having the large amount of light.

Figure 3:
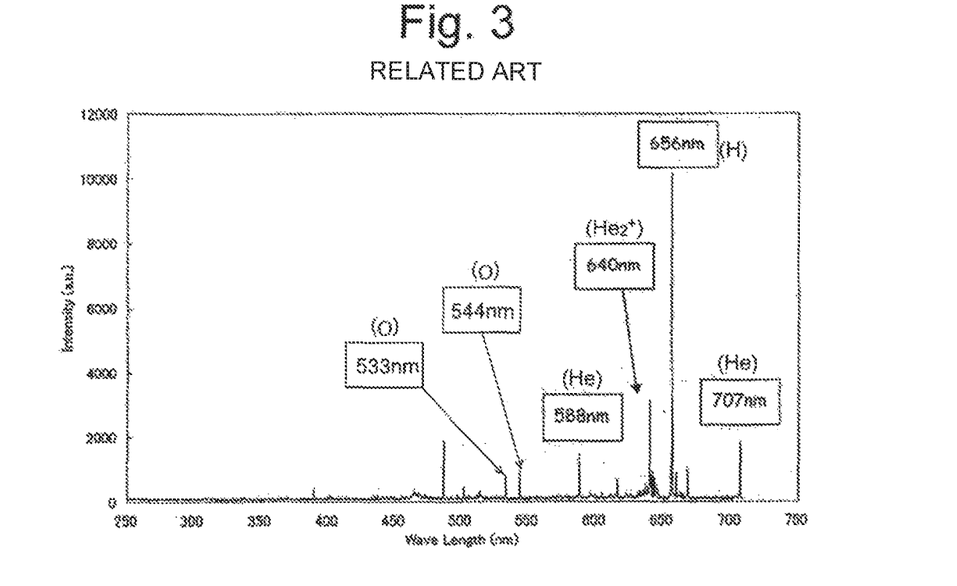
FIG. 3 is a view illustrating the emission spectrum of helium plasma generated in a conventional discharge ionization current detector.

In contrast, FIG. 3 illustrates the emission spectrum of the helium plasma in a case where the cylindrical pipe 24 is formed of fused quartz glass having a hydroxyl group content of 200 ppm or higher under the same conditions except the forming condition of the cylindrical pipe 24. Similarly, in this emission spectrum, the emission line (at the wavelength of 656 nm) of the hydrogen atom that is impurity emerges besides the emission lines (at the wavelengths of 588 nm and 707 nm) of the helium atom and the emission line (at the wavelength of 640 nm) of the helium molecular ion ($He_2^+$). Furthermore, the emission lines (at the wavelengths of 533 nm and 544 nm) of the oxygen atom emerge, which do not emerge in the emission spectrum in FIG. 2. In addition, the intensity of the emission line at the wavelength of 656 nm increases and more dominant than that of the emission lines at the wavelength of 640 nm. This represents that the hydroxyl group (OH) included in the quartz glass is resolved into oxygen (O) or hydrogen (H) and is released through exposure of the quartz glass to the helium plasma. Thus generated helium plasma has a high impurity concentration, and the vacuum ultraviolet light emitted by the helium plasma has the small amount of light and becomes unstable.

As described above, the helium plasma generated in the discharge ionization current detector under the aforementioned conditions, has a low impurity concentration, and as a result, the helium plasma emits the stable vacuum ultraviolet light having the large amount of light, so that the precision and reproducibility of measurements by means of the discharge ionization current detector are improved.

Also, the aforementioned conditions are set in advance as a results of experiment or the like, after that the discharge ionization current detector having the same performance can be obtained without using the spectrum analyzer 42 (that is, even when the constitution illustrated in FIG. 1 is employed). In other words, after the purity and the flow rate of the helium gas are set to a predetermined amount (or value), a low-frequency voltage having amplitude and/or frequency that the intensity of the emission line at the wavelength of 640 nm reaches the maximum may be supplied based on the experiment results. Similarly, after the amplitude and the frequency of the low-frequency voltage are set to a predetermined value, the purity and/or the flow rate of the helium gas that the intensity of the emission line at the wavelength of 640 nm reaches the maximum may be set based on the results of experiment.

The use of the discharge ionization current detector having the constitution illustrated in FIG. 4 provides the following advantages. Generally, when the discharge ionization current detector is used for a long period of time, the quality of the helium plasma generated in the detector is varied along with time-dependent deterioration of each component or the like. As a result, there is a risk that, the helium plasma having the emission spectrum, in which the intensity of the emission line at the wavelength of 640 nm becomes higher than that of the emission lines at other wavelengths in a range of wavelengths of 250 to 700 nm, cannot be generated.

However, with the constitution illustrated in FIG. 4, the user can analyze the sample components in consideration of the emission state of the vacuum ultraviolet light of the helium plasma. Here, for example, the criteria for determining the quality of the emission state may be set in advance. Comparing the criteria with the result of measurements by the spectrum analyzer enables appropriate determination. The criteria may be made up of the comparison of the intensity of the emission line at the wavelength of 640 nm with that of the emission line at other wavelengths, or only the magnitude of the intensity of the emission line at the wavelength of 640 nm. Also, for example, the criteria may be provided such that the intensity of the emission line at the wavelength of 640 nm is higher than that of the emission line of the hydrogen atom having a wavelength of 656 nm (for example, approximately three times). When the user determines that the emission state is favorable, based on the aforementioned criteria, the user analyzes the sample components, and when the user determines that the emission state of the vacuum ultraviolet light is unfavorable, the user can suspend the analysis of the sample components and perform the aforementioned adjustment.

Herein, the emission spectrum analyzer that copes with the range of wavelengths of 250 to 700 nm (ultraviolet light to visible light) is less expensive than a large-size, high-priced vacuum ultraviolet spectrometer for directly observing the vacuum ultraviolet light, and is desirable in terms of manufacturing cost of the detector.

Figure 5:
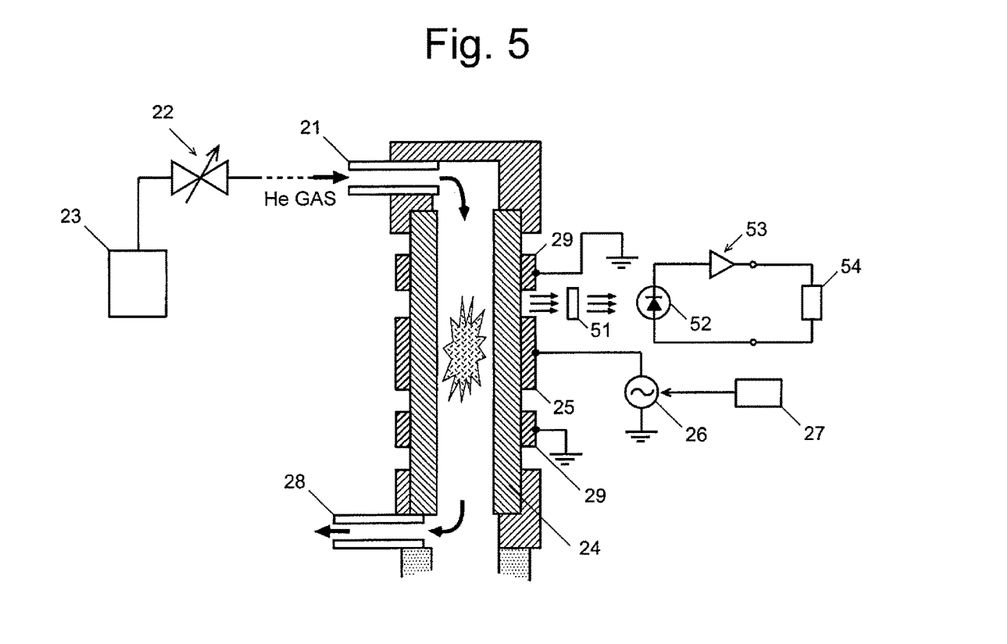
FIG. 5 is a view illustrating the schematic configuration of the plasma generating section of the discharge ionization current detector in another embodiment of the present invention.

Besides the FIG. 4, FIG. 5 illustrates constitution as the device for verifying t the emission state of the helium plasma. In this constitution, after the light emitted by the helium plasma is passed through a wavelength filter 51, the light enters a photodiode 52. The photodiode 52 generates the electric charge amount depending on the intensity of the incident light. This allows the electric current to flow, and the electric current is amplified by the amplifier 53, and measured by a current/voltage converter 54 as voltage. The wavelength filter 51 filters through the emission line at the wavelength of 640 nm. With the aforementioned constitution, the emission state of the helium plasma also can be verified by measuring the intensity of the emission line at the wavelength of 640 nm. Also, the manufacturing cost of the detector is reduced, compared with a case of using the aforementioned emission spectrum analyzer.

Figure 6:
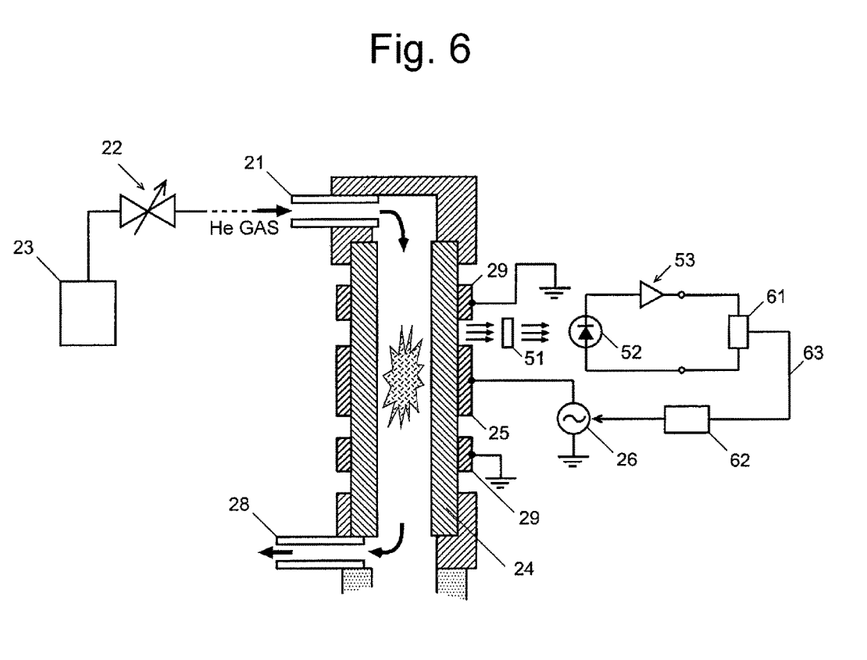
FIG. 6 is a view illustrating the schematic configuration of the plasma generating section of the discharge ionization current detector in another embodiment of the present invention.

Furthermore, FIG. 6 illustrates the constitution in which the voltage and frequency of the low-frequency dielectric barrier discharge are automatically controlled based on the emission state of the helium plasma. In this the constitution, a current/voltage converter 61 and a controller 62 are connected with a control line 63 so as to communicate with each other. The controller 62 controls the amplitude and/or frequency of the voltage of the alternating-current power supply 26 based on the measurement results by the current/voltage converter 61. Herein, the control is made such that the intensity of the emission line at the wavelength of 640 nm is higher than that of the emission lines of other wavelengths and is constant, with respect to the light emitted by the helium plasma. When the intensity of the emission line at the wavelength of 640 nm remains constant by such control, the emission state of the vacuum ultraviolet light of the helium plasma can be further stabilized, and the precision and reproducibility of measurements by means of the detector can be further improved.

Attention needs to be paid in order to prevent the excessive increase in the plasma temperature of the helium plasma when the amplitude and/or frequency of the voltage is controlled. This is because when the temperature increases too high, the impurity leaked from the surface of the dielectric member that forms the cylindrical pipe 24 also increases. In view of this point, it is preferable that the amplitude ranges 1 to 10 kV, and the frequency ranges 1 to 50 kHz.

It is noted that the controller 62 may control the helium purifier 23 and adjust the purity of the helium gas based on the measurement results of the current/voltage converter 61, so that the intensity of the emission line at the wavelength of 640 nm, with respect to the light emitted by the helium plasma, is higher than the that of the emission lines of other wavelengths and is constant. Similarly, the controller 62 may control the valve 22 and adjust the flow rate of the helium gas based on the measurement results of the current/voltage converter 61, so that the intensity of the emission line at the wavelength of 640 nm, with respect to the light emitted by the helium plasma, is higher than the that of the emission lines at other wavelengths and is constant.

REFERENCE SIGNS LIST

10 . . . Discharge Ionization Current Detector
20 . . . Plasma Generating Section
21 . . . Gas Introduction Port
22 . . . Valve
23 . . . Helium Purifier
24 . . . Cylindrical Pipe
25 . . . Discharge Electrode
26 . . . Alternating-Current Power Supply
27, 62 . . . Controller
28, 37 Exhaust Port
29 . . . Grounding Electrode
30 . . . Ion Collecting Section
31 . . . Ion Collecting Electrode
32 . . . Bias Electrode
33 . . . Insulating Member
34 . . . Capillary
35 . . . Direct-Current Power Source
36 . . . Amplifier
41 . . . Optical Fiber
42 . . . Spectrum Analyzer
51 . . . Wavelength Filter
52 . . . Photodiode
53 . . . Amplifier
54, 61 . . . Current/Voltage Converter
63 . . . Control Line

The invention claimed is:

1. A tuning method for a discharge ionization current detector for a gas analyzer configured to utilize helium plasma generated by low-frequency dielectric barrier discharge, comprising:
adjusting at least one of purity of introduced helium gas, a flow rate of the introduced helium gas, an amplitude of voltage of the low-frequency dielectric barrier discharge, and a frequency of the voltage of the low-frequency dielectric barrier discharge so that light having a wavelength of 640 nm, which is the emission line of the helium molecular ion $He_2^+$, has the highest intensity amongst all light emitted by the helium plasma that falls within a range of wavelengths of 250 nm to 700 nm.

2. A discharge ionization current detector for a gas analyzer configured to utilize helium plasma generated by low-frequency dielectric barrier discharge, comprising:

a) a helium gas introducing section configured to introduce helium gas;
b) a voltage adjusting section configured to adjust an amplitude or a frequency of low-frequency voltage applied to a discharge electrode used for the low-frequency dielectric barrier discharge;
c) a light detecting section configured to detect intensity of light for every wavelength in a range of wavelengths of 250 nm to 700 nm with respect to light emitted by the helium plasma; and
d) a control section configured to control the voltage adjusting section in such a manner that light having a wavelength of 640 nm, which is the emission line of the helium molecular ion $He_2^+$, reaches the highest intensity amongst all light emitted by the helium plasma that falls within the range of the wavelengths.

3. The discharge ionization current detector according to claim 2, further comprising:
e) a helium gas purity adjusting section configured to adjust purity of the introduced helium gas, and
f) a helium gas flow rate adjusting section configured to adjust a flow rate of the introduced helium gas,
wherein the control section is configured to control at least one of the helium gas purity adjusting section and the helium gas flow rate adjusting section in such a manner that light having the wavelength of 640 nm reaches the highest intensity amongst all light emitted by the helium plasma that falls within the range of the wavelengths.

4. The discharge ionization current detector according to claim 2,
wherein the control section is further configured to control the voltage adjusting section in such a manner that the intensity of the light having the wavelength of 640 nm remains constant.

5. The discharge ionization current detector according to claim 3,
wherein the control section is further configured to control the voltage adjusting section in such a manner that the intensity of the light having the wavelength of 640 nm remains constant.

6. A discharge ionization current detector for a gas analyzer configured to utilize helium plasma generated by low-frequency dielectric barrier discharge, comprising:
a helium gas introducing section configured to introduce helium gas; and
a low-frequency voltage applying section configured to apply low-frequency voltage to a discharge electrode used for the low-frequency dielectric barrier discharge, in which the low-frequency voltage is determined in such a manner that light having a wavelength of 640 nm, which is the emission line of the helium molecular ion $He_2^+$, reaches the highest intensity amongst all light emitted by the helium plasma that falls within a range of wavelengths of 250 nm to 700 nm.

7. A discharge ionization current detector for a gas analyzer configured to utilize helium plasma generated by low-frequency dielectric barrier discharge, comprising:
a low-frequency voltage applying section configured to apply low-frequency voltage to a discharge electrode used for the low-frequency dielectric barrier discharge; and
a helium gas introducing section configured to introduce helium gas, whose purity or flow rate is determined in such a manner that light having a wavelength of 640 nm, which is the emission line of the helium molecular ion $He_2^+$, reaches the highest intensity amongst all light emitted by the helium plasma that falls within a range of wavelengths of 250 nm to 700 nm.

* * * * *